US011206053B2

(12) United States Patent
Moran et al.

(10) Patent No.: US 11,206,053 B2
(45) Date of Patent: *Dec. 21, 2021

(54) WEARABLE ARTICLE WITH MULTI-FREQUENCY WIRELESS COMMUNICATION

(71) Applicant: NIKE, Inc., Beaverton, OR (US)

(72) Inventors: Douglas Moran, Beaverton, OR (US); Holli Pheil, Portland, OR (US); Drew McLain Skeels, Portland, OR (US); Allison Walters, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/113,199

(22) Filed: Dec. 7, 2020

(65) Prior Publication Data

US 2021/0194526 A1 Jun. 24, 2021

Related U.S. Application Data

(63) Continuation of application No. 15/825,466, filed on Nov. 29, 2017, now Pat. No. 10,862,522, which is a
(Continued)

(51) Int. Cl.
*H04B 1/3827* (2015.01)
*H04B 5/00* (2006.01)
(Continued)

(52) U.S. Cl.
CPC ........... *H04B 1/385* (2013.01); *A43B 3/0005* (2013.01); *A61B 5/6807* (2013.01);
(Continued)

(58) Field of Classification Search
CPC ........... H04W 4/80; H04W 4/90; H04W 4/02; H04W 88/02; H04W 12/06; H04W 4/70;
(Continued)

(56) References Cited

U.S. PATENT DOCUMENTS 7,804,886 B2  9/2010 Silver et al.
8,253,586 B1 * 8/2012 Matak ............... G06F 17/00
340/870.07
(Continued)

FOREIGN PATENT DOCUMENTS

CN     2722450     8/2005
CN   101454812     6/2009
(Continued)

OTHER PUBLICATIONS

U.S. Appl. No. 15/577,812 U.S. Pat. No. 10,211,870, filed Nov. 29, 2017, Wearable Article with Multi-Frequency Wireless Communication.
(Continued)

*Primary Examiner* — Ajibola A Akinyemi
(74) *Attorney, Agent, or Firm* — Schwegman Lundberg & Woessner, P.A.

(57) ABSTRACT

A wearable article, system, and methods may include a structure configured to enclose a human body part. A first antenna, positioned with respect to the structure, is tuned to communicate, while the wearable article is being worn, according to a first wireless communication modality with a first external antenna. A second antenna, positioned with respect to the structure, is tuned to communicate according to a second wireless communication modality with a second external antenna different than the first external antenna, the second communication modality being different than the first communication modality. A transceiver, coupled to at least one of the first antenna and the second antenna, is configured to communicate via one of the first and second antennas based, at least in part, on the one of the first and second antennas coming into wireless communication contact with a corresponding one of the first and second external antennas.

20 Claims, 10 Drawing Sheets

Related U.S. Application Data continuation of application No. PCT/US2016/034705, filed on May 27, 2016.

(60) Provisional application No. 62/168,189, filed on May 29, 2015.

(51) Int. Cl.
| | | |
|---|---|---|
| *A43B 3/00* | (2006.01) | |
| *H04B 5/02* | (2006.01) | |
| *H04W 4/80* | (2018.01) | |
| *A61B 5/00* | (2006.01) | |
| *G06K 19/077* | (2006.01) | |
| *H04W 4/21* | (2018.01) | |

(52) U.S. Cl.
CPC ..... *G06K 19/07767* (2013.01); *H04B 5/0031* (2013.01); *H04B 5/0087* (2013.01); *H04B 5/02* (2013.01); *H04W 4/80* (2018.02); *H04W 4/21* (2018.02)

(58) Field of Classification Search
CPC ..... H04W 4/021; H04W 12/08; H04W 4/023; H04W 76/14; H04W 4/06; H04W 4/21; H04W 76/11; H04W 76/50; H04W 84/18; H04W 84/12; H04W 88/184
USPC .......................................... 455/41.2
See application file for complete search history.

(56) References Cited

U.S. PATENT DOCUMENTS

| | | | |
|---|---|---|---|
| 8,371,501 | B1 | 2/2013 | Hopkins |
| 10,211,870 | B2 | 2/2019 | Moran et al. |
| 10,862,522 | B2 | 12/2020 | Moran et al. |
| 2004/0075613 | A1* | 4/2004 | Jarmuszewski ......... H01Q 9/26 343/702 |
| 2009/0016418 | A1* | 1/2009 | Silver ................... H04B 1/385 375/220 |
| 2012/0019363 | A1 | 1/2012 | Fein |
| 2012/0302183 | A1* | 11/2012 | Pescod ................ H04B 7/0608 455/78 |
| 2014/0187160 | A1 | 7/2014 | Prencipe |
| 2018/0078207 | A1 | 3/2018 | Moran et al. |
| 2018/0167097 | A1 | 6/2018 | Moran et al. |

FOREIGN PATENT DOCUMENTS

| | | |
|---|---|---|
| CN | 101479572 | 7/2009 |
| CN | 101689041 | 3/2010 |
| CN | 103170105 | 6/2013 |
| CN | 107667476 | 2/2018 |
| WO | 2012112938 | 8/2012 |
| WO | 2016196310 | 12/2016 |

OTHER PUBLICATIONS

U.S. Appl. No. 15/825,466 U.S. Pat. No. 10,862,522, filed Nov. 29, 2017, Wearable Article with Multi-Frequency Wireless Communication.
"International Application Serial No. PCT US2016 034705, International Search Report dated Aug. 24, 2016", 3 pgs.
"International Application Serial No. PCT US2016 034705, Written Opinion dated Aug. 24, 2016", 14 pgs.
"International Application Serial No. PCT US2016 034705, International Preliminary Report on Patentability dated Dec. 14, 2017", 16 pgs.
"U.S. Appl. No. 15/577,812, Non Final Office Action dated May 31, 2018", 10 pgs.
"U.S. Appl. No. 15 577,812, Examiner Interview Summary dated Jul. 17, 2018", 3 pgs.
"European Application Serial No. 16804131.7, Response filed Jul. 19, 2018 to Communication Pursuant to Rules 161(2) and 162 dated Jan. 24, 2018", 13 pgs.
"U.S. Appl. No. 15/577,812, Respnse filed Aug. 30, 18 to Non Final Office Action dated May 31, 2018", 10 pgs.
"U.S. Appl. No. 15/577,812, Notice of Allowance dated Oct. 1, 2018", 5 pgs.
"U.S. Appl. No. 15/577,812, 312 Amendment filed Nov. 1, 2018", 9 pgs.
"U.S. Appl. No. 15/577,812, PTO Response to Rule 312 Communication dated Nov. 15, 2018", 2 pgs.
"U.S. Appl. No. 15/825,466, Non Final Office Action dated Nov. 23, 2018", 12 pgs.
"U.S. Appl. No. 15/825,466, Examiner Interview Summary dated Jan. 8, 2019", 3 pgs.
"European Application Serial No. 16804131.7, Extended European Search Report dated Mar. 8, 2019", 7 pgs.
"U.S. Appl. No. 15/825,466, Response filed Mar. 25, 19 to Non Final Office Action dated Nov. 23, 2018", 9 pgs.
"U.S. Appl. No. 15/825,466, Final Office Action dated Jul. 1, 2019", 13 pgs.
"U.S. Appl. No. 15/825,466, Examiner Interview Summary dated Jul. 31, 2019", 3 pgs.
"U.S. Appl. No. 15/825,466, Response filed Oct. 1, 2019 to Final Office Action dated Jul. 1, 2019", 9 pgs.
"European Application Serial No. 16804131.7, Response filed Oct. 7, 2019 to Extended European Search Report dated Mar. 8, 2019", 15 pgs.
"Chinese Application Serial No. 201680031532.9, Office Action dated Sep. 23, 2019", W English Translation, 30 pgs.
"U.S. Appl. No. 15/825,466, Non Final Office Action dated Dec. 18, 2019", 13 pgs.
"U.S. Appl. No. 15 825,466, Examiner Interview Summary dated Feb. 26, 2020", 3 pgs.
"European Application Serial No. 16804131.7, Communication Pursuant to Article 94(3) EPC dated Mar. 30, 2020", 5 pgs.
"Chinese Application Serial No. 201680031532.9, Response filed Mar. 31, 20 to Office Action dated Sep. 23, 2019", w English claims, 53 pgs.
"U.S. Appl. No. 15/825,466, Response filed May 18, 20 to Non Final Office Action dated Dec. 18, 2019", 9 pgs.
"European Application Serial No. 16804131.7, Response filed Jun. 24, 20 to Communication Pursuant to Article 94(3) EPC dated Mar. 30, 2020", 11 pgs.
"U.S. Appl. No. 15/825,466, Notice of Allowance dated Jul. 31, 2020", 8 pgs.
"Chinese Application Serial No. 201680031532.9, Office Action dated Jul. 10, 2020", w English translation, 18 pgs.
"European Application Serial No. 16804131.7, Communication Pursuant to Article 94(3) EPC dated Sep. 8, 2020", 3 pgs.
"U.S. Appl. No. 15/825,466, Notice of Allowability dated Sep. 16, 2020", 2 pgs.
"U.S. Appl. No. 15/825,466, Notice of Allowability dated Nov. 12, 2020", 2 pgs.
"European Application Serial No. 16804131.7, Response filed Feb. 24, 2021 to Communication Pursuant to Article 94(3) EPC dated Sep. 8, 2020", 13 pgs.
"Chinese Application Serial No. 201680031532.9, Response filed Nov. 10, 2020 to Office Action dated Jul. 10, 2020", w English claims, 45 pgs.
"Chinese Application Serial No. 201680031532.9, Office Action dated Apr. 6, 2021", w English Translation, 15 pgs.

* cited by examiner

WEARABLE ARTICLE WITH MULTI-FREQUENCY WIRELESS COMMUNICATION

PRIORITY CLAIM

This application claims the benefit of priority of U.S. Provisional Patent Application Ser. No. 62/168,189, filed on May 29, 2015, which is incorporated by reference herein in its entirety.

TECHNICAL FIELD

The subject matter disclosed herein generally relates to a wearable article configured for multi-frequency wireless communication in an integrated wireless environment.

BACKGROUND

Radio frequency identification (RFID) systems have been incorporated into wearable articles, such as footwear, shirts, pants, hats, and the like, and other goods and items to provide item tracking for operations such as inventory tracking and the like. For instance, a passive RFID tag may be attached to an article of apparel. The RFID tag may be energized by an RFID tag reader remotely as the RFID tag passes through stations in, for instance, a supply chain and within a store. In that way, the article of apparel may be tracked and inventory updated appropriately without necessarily requiring human intervention to conduct the tracking.

BRIEF DESCRIPTION OF THE DRAWINGS

Some embodiments are illustrated by way of example and not limitation in the figures of the accompanying drawings.

DETAILED DESCRIPTION

Example methods and systems are directed to a wearable article configured for multi-frequency wireless communication in an integrated wireless environment. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

Comparatively simple use cases of inventory tracking using RFID are possible in part because articles of apparel, for instance, present little impediment to the transmittal of wireless signals conventionally used in RFID tags. Various substances and materials, including water and other constituent parts of humans, animals, and clothing, among other things, may be impermeable or otherwise inhibiting of wireless signals in the 900 MHz bands that are normally tuned for transmission through air. Thus, such RFID tags or other wireless transmitters in the 900 MHz bands may be of substantially reduced range and effectivity while the article of apparel is actually being worn on a person's body. The same applies to different surfaces that may commonly be found in various environments such as buildings and public spaces, including flooring, shelving, electronics, and the like.

As such, the use of RFID technology in a wearable article that is conventionally used for inventory tracking may be of limited use when the wearable article is being worn by a user in integrated wireless environments, such as stores and entertainment complexes. A wearable article has been developed along with an accompanying integrated wireless environment that allows for rich RF communication from antennas located in the wearable article. Because of the wireless communication provided by the wearable article, the integrated wireless environment provides data transfer to and from the wearable article, allowing for personalized greetings and recommendations and tracking of the wearable article.

The wearable article provides multiple antennas for wireless communication. One antenna is a UHF antenna for communication in the 900 MHz bands that is not tuned to the presence of an animal body. A second antenna is a UHF antenna for communication in the 900 MHz bands that tuned to the presence of an animal body. In various examples, only the body-tuned UHF antenna is included. In further examples, a third antenna is tuned to communicate in bands around 13.5 MHz or according to other wireless communication standards. The various antennas may be controlled and either actively or passively coordinated to prevent interference between one another by a single transmitter circuit.

Figure 1:
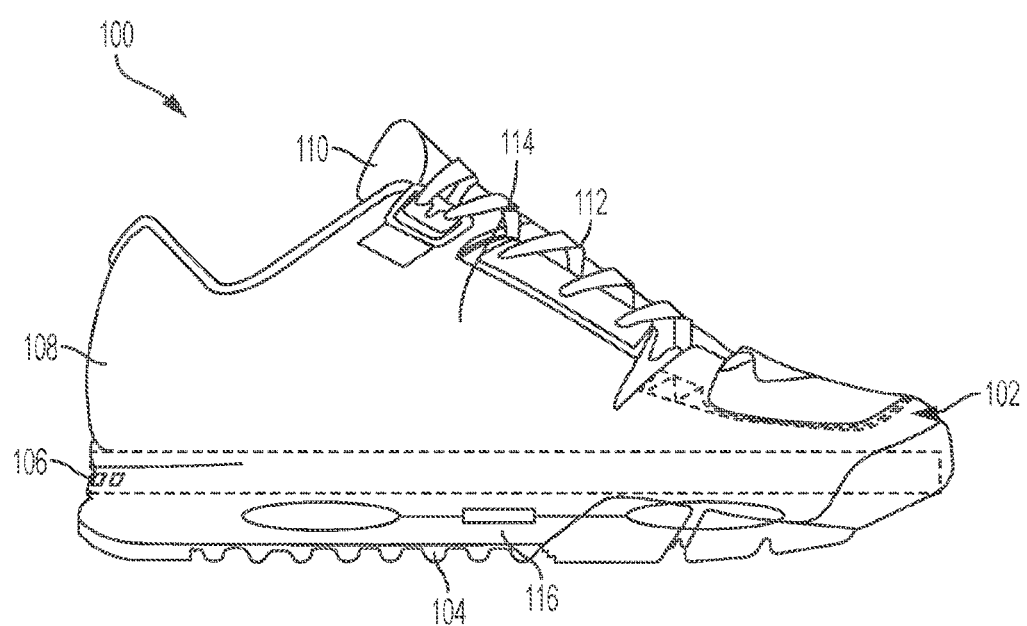
FIG. 1 is a cutaway depiction of a wearable article, in an example embodiment.

FIG. 1 is a depiction of a wearable article 100, including components contained within the wearable article 100 and not necessarily visible from perspective illustrated, in an example embodiment. As illustrated, the wearable article 100 is an article of footwear, specifically a shoe. However it is to be understood that while the principles described herein are with specific reference to the wearable article 100, the principles described herein may be applied to any suitable article of apparel, without limitation.

The wearable article 100 includes a structure 102 including an outsole 104 designed to come into contact with a surface, such as the ground or a floor, an insole 106 configured to seat a human foot, an upper section 108 configured to enclose the human foot, and a tongue 110 configured to facilitate securing the wearable article 100 to the human foot via laces 112. The outsole 104 and/or the insole 106 may be configured within a middle section 114 to seat and secure the arch of a human foot. It is to be recognized that this is a simplified depiction of a conventional article of footwear and that various articles of footwear may incorporate any of a variety of components or features. Further, certain articles of apparel 100 may not incorporate all or these features or may include these features in other formats (e.g., a sandal may incorporate the outsole 104 and a reconfigured upper section 106 and no insole 106, tongue 110, and laces 112). It is contemplated that the principles disclosed herein will be applicable and adaptable to any of a range of articles of apparel 100.

The wearable article 100 further includes a radio frequency ("RF") communication circuit 116. The RF communication circuit 116 may incorporate some conventional features of RFID tags known in the art as well as the various features disclosed herein. As illustrated, the RF communication circuit 116 is positioned within the middle section 114, seated within and enclosed by the outsole 104. However, in various examples the RF communication circuit 116 may be positioned between the outsole 104 and insole 106, within and enclosed by the insole 106, within the upper section 108, such as on a side of the article of apparel, or within the tongue 110.

Ultra high frequency (UHF) wireless communication may vary in operation frequency between and among certain countries, but in general may be understood to occur over the range of approximately 300 megahertz (MHz) to approximately three (3) gigahertz (GHz). Certain regions throughout the world utilize a variety different of industrial, scientific, and medical (ISM) bands for UHF communications. Certain ISM bands are centered around approximately 900 MHz, with the center frequencies of those bands falling generally within the range of approximately 869 MHz to approximately 915 MHz.

The ISM bands and other regional and international communication bands clustered around approximately 900 MHz (herein after "the 900 MHz bands") may be useful in a variety of circumstances, including but not limited to radio frequency identification (RFID) tags, chips, and the like, as known in the art. An RFID tag with a UHF antenna that is positioned in a shirt, for instance, may communicate to a suitable range in directions away from the body of the wearer of the shirt but may not communicate in directions that pass through the wearer. An RFID tag in a shoe may be effectively unable to communicate at all while the shoe is being worn if the tag is in the sole or heel of the shoe. Even if the RFID tag is positioned higher in the shoe, such as in the tongue, effective communication may still be limited both by the presence of the foot and the proximity of the tag to the ground. Circumstances in which RFID tags are attached to a shoe intentionally place the RFID at a distinct distance from the foot of the wearer to maintain the ability to communicate at an effective distance.

Actions taken to tune a UHF antenna to communicate effectively through a human body may, however, reduce the effectivity of the UHF antenna when the article of apparel is not being worn by a person. Additionally, the circumstances of wearing the article of apparel may place the UHF antenna away from the body, in the case of an overly-large shirt, for instance. Thus, to tune the antenna to the body of the wearer may result in reduced effectiveness under the circumstances in which the article of apparel isn't being worn.

Figure 2:
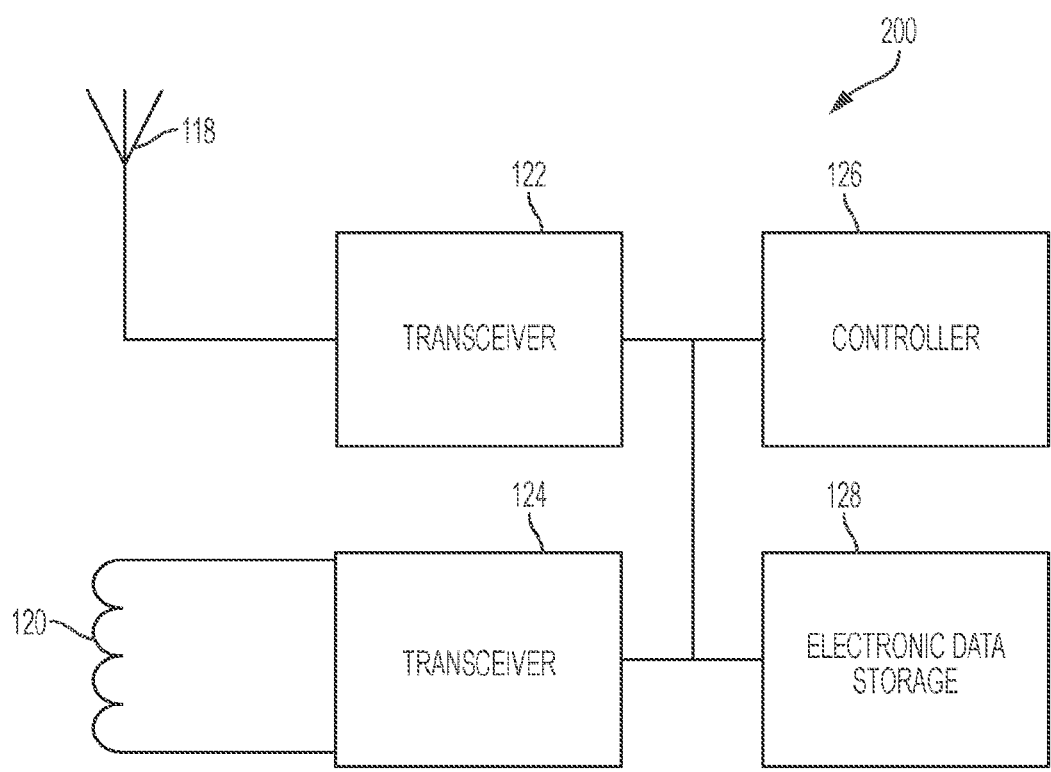
FIG. 2 is a block diagram of an RF communication system of a wearable article, in an example embodiment.

FIG. 2 is a block diagram of an RF communication system 200 of the wearable article 100, in an example embodiment. In an example, the RF communication system 200 includes a first antenna 118 that is tuned to transmit UHF signals effectively through air and a second antenna 122 that is configured to communicate according to high frequency (HF) and/or near field communication (NFC) at approximately 13.5 MHz. In an example, the first antenna 118 is configured to communicate according to a UHF standard, including any one or more of Gen2 or ISO18000-6C (again including versions of those standards that are past, current, or that may be developed). In an example, the second antenna 120 is configured to communicate according to any one or more standards including ISO14443B, ISO1443A NFC Type 4, and ISO 15693 (including contemporary and previous versions of those standards as well as versions of those standards that are yet to be promulgated or adopted).

The RF communication circuit 116 further includes first and second transceivers 122, 124 each individually coupled to a respective one of the antennas 118, 120 and configured to communicate according to the wireless modality of the corresponding antenna 118, 120. Each transceiver 122, 124 may include componentry such as a voltage rectifier and a modulator as appropriate for the respective antenna 118, 120. The transceivers 122, 124 are coupled to an electronic data storage 126, such as an electrically erasable programmable read-only memory ("EEPROM") circuit, non-volatile read-only memory, or read/write memory circuit, such as various types of random access memory ("RAM") known in the art, and an optional controller 128. In various implementations, individual ones of the transceivers 122, 124 may be combined as or with a single transceiver, such as the transceiver 122, providing transmitting and receiving functionality for multiple antennas. In an example, the electronic data storage 126 includes a unique identifier of the wearable article 100 among other information as desired and provides for a unified memory module for data that may be transmitted by and stored from the transceivers 122, 124.

In various examples, the wearable article 100 includes one or more sensors, such as an accelerometer or step counter, among a variety of other sensors or other data gathering implements known in the art. Those sensors may store information to the electronic data storage 126 during use of the wearable article 100 by a wearer. Thus, for instance, the electronic data storage 126 may store a number of steps taken during the life of the article of apparel as well as additional information about how and when the wearable article 100 has been used. As will be disclosed herein that information may be transmitted by the RF communication system 200 for use in interacting with a wearer of the wearable article 100, particularly when the article of apparel is within an integrated wireless environment.

The RF communication system 200 as illustrated is a passive RF communication system 200 and, as a result, draws energy from received RF signals rather than an internal power source or supply, such as a battery or energy harvesting system. However, various examples of the RF communication system 200 may be active and incorporate an internal power source or supply and relatively power intensive componentry not illustrated herein.

As illustrated, the RF communication system 200 includes the controller 126 and the electronic data storage 128 as well as the second antenna 120 as components of the RF communication circuit 116. As such, in an example, the second antenna 120, controller 126, and electronic data storage 128 are on a single substrate. In such an example, the first antenna 118 is located remote to the RF communication circuit 116 but is coupled to the RF communication circuit 116 with a conductor that passes through a structure of the wearable article 100. In the illustrated example, the controller 126 and electronic data storage 128 provide a unified system for the operation of both of the transceivers 122, 124.

In an alternative example, the RF communication circuit 166 does not include the first transceiver 116. In such an example, the first antenna 118 and the first transceiver 112 are located along with a separate controller and/or electronic data storage on a separate substrate or RF tag. In such an example, RF communication system 200 includes two separate and independent subsystems, each configured to communicate according to a different communication modality with separate components. Additionally or alternatively, the separate systems may be coupled to one another and coordinate, such as by sharing electronic data, but otherwise may operate separately and independently.

FIGS. 3A-3F are images of the wearable article 100, showing example locations of one or both of the first antenna 118 and the second antenna 120, in an example embodiment. The positions of the antennas 118, 120 illustrated are non-limiting and it is to be recognized and understood that various alternative or additional locations are contemplated. Furthermore, individual implementations of the wearable article 100 may utilize any combination of locations of the antennas 118, 120. Each of these implementations are designed and configured to allow for wireless communications at useful and typical ranges for their representative modalities, including when the wearable article 100 is being worn by a user.

Figure 3A:
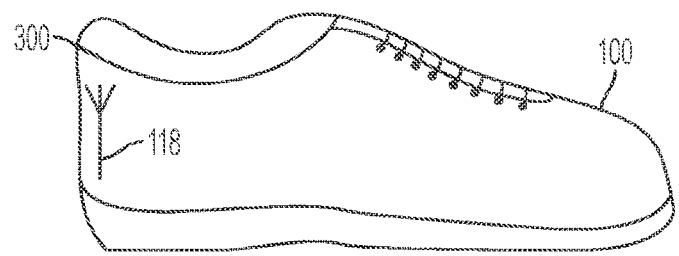
FIGS. 3A-3F are images of a wearable article, showing example locations of one or both of a first antenna and a second antenna, in an example embodiment.

In FIG. 3A, the first antenna 118 is positioned in the heel 300. In such a configuration, when the wearable article 100 is flexed as from taking a normal step the first antenna 118 is presented generally upward. As a result, during a normal step the first antenna 118 may be exposed to another antenna that may be above the wearer of the wearable article 100. Owing to UHF communications conventionally having a range of tens of feet or five or more meters, the first antenna 118 may communicate with antennas that are positioned at a moderate distance from the wearable article 100. Thus, as the wearer of the wearable article 100 moves around an integrated wireless environment disclosed herein, the first antenna 118 may tend to regularly be exposed to antennas that are positioned both overhead and to the side of the wearable article 100.

Figure 3B:
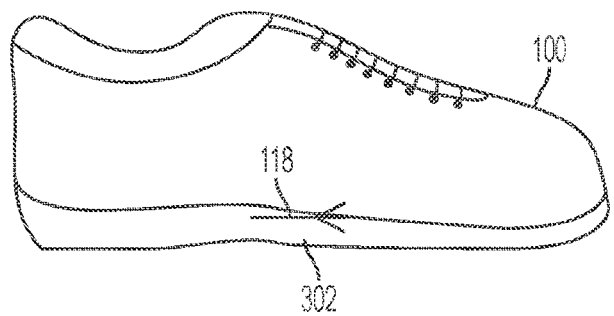

In FIG. 3B, the first antenna 118 is positioned in the midsole 302 region of the outsole 104. In such an example, the first antenna 18 may be tuned to transmit UHF signals effectively through a human body (see, e.g., Santiago et al, "Broadband UHF RFID Passive Tag Antenna for Near-Body Applications", *IEEE Antennas and Wireless Propagation Letters Vol.* 12, (2013), pp. 136-139, incorporated herein by reference in its entirety). As a result, the first antenna 118 may maintain an effective transmission range despite transmitting through the foot of a wearer of the wearable article 100.

Figure 3C:
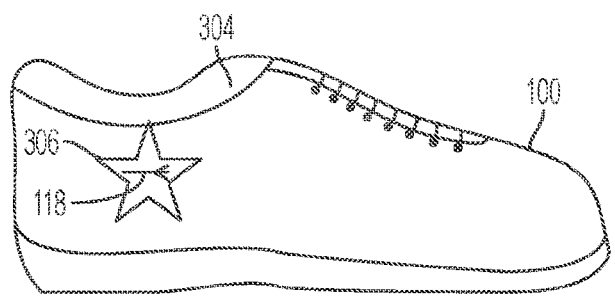

In FIG. 3C, the first antenna 118 is positioned an a side 304 of the wearable article 100. In an example, the first antenna 118 is formed in the shape of a decorative element or a brand logo. Thus, in such an example, the first antenna 118 may comprise the decorative element itself or may be positioned behind or otherwise be obscured by the decorative element with the decorative element not itself necessarily being an antenna.

Figure 3D:
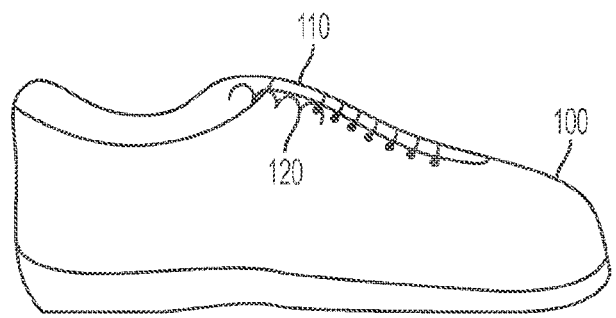

In FIG. 3D, the second antenna 120 is positioned on or in the tongue 110 of the wearable article 110. In an example, the positioning of the second antenna 120 in the tongue 110 may allow for the second antenna 120 to communicate according to the HF ISO 15693 modality through the wearable article 100 to the another HF antenna positioned in the floor, a mat or a walking surface in general as well as communicate with HF antennas that may be positioned a relatively short distance above or to the side of the wearable article 100. In an example, the second antenna 120 may communicate with HF antennas that are approximately one foot or thirty centimeters above the tongue 110, e.g., that may be positioned in a counter a wearer may walk up to or a desk at which the wearer may sit.

Figure 3E:
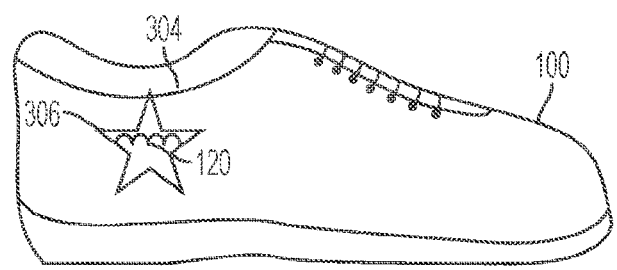

In FIG. 3E, the second antenna is positioned on the side 304 of the wearable article 100. In an example, the second antenna 120 is formed in the shape of the decorative element 300 or brand logo. Thus, in such an example, the second antenna 120 may comprise the decorative element itself or may be positioned behind or otherwise be obscured by the decorative element with the decorative element not itself necessarily being an antenna.

Figure 3F:
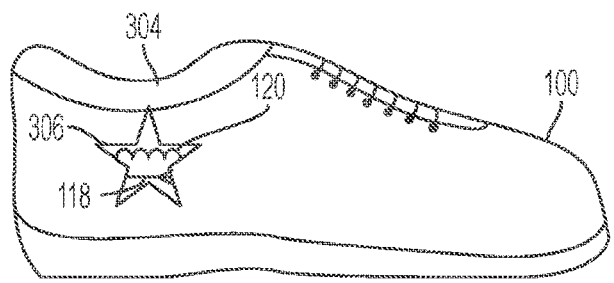

In FIG. 3F, the first antenna 118 and the second antenna 120 are combined on the side 304 of the wearable article 100 in the form of the decorative element or brand logo. In such an example, the first antenna 118 may form a first portion of the decorative element and the second antenna 120 may form a second portion of the decorative element. Alternatively, the decorative element may be formed from one of the antennas 118, 120 while the other of the antennas 118, 120 is positioned behind or otherwise in part obscured by the decorative element.

Figure 4:
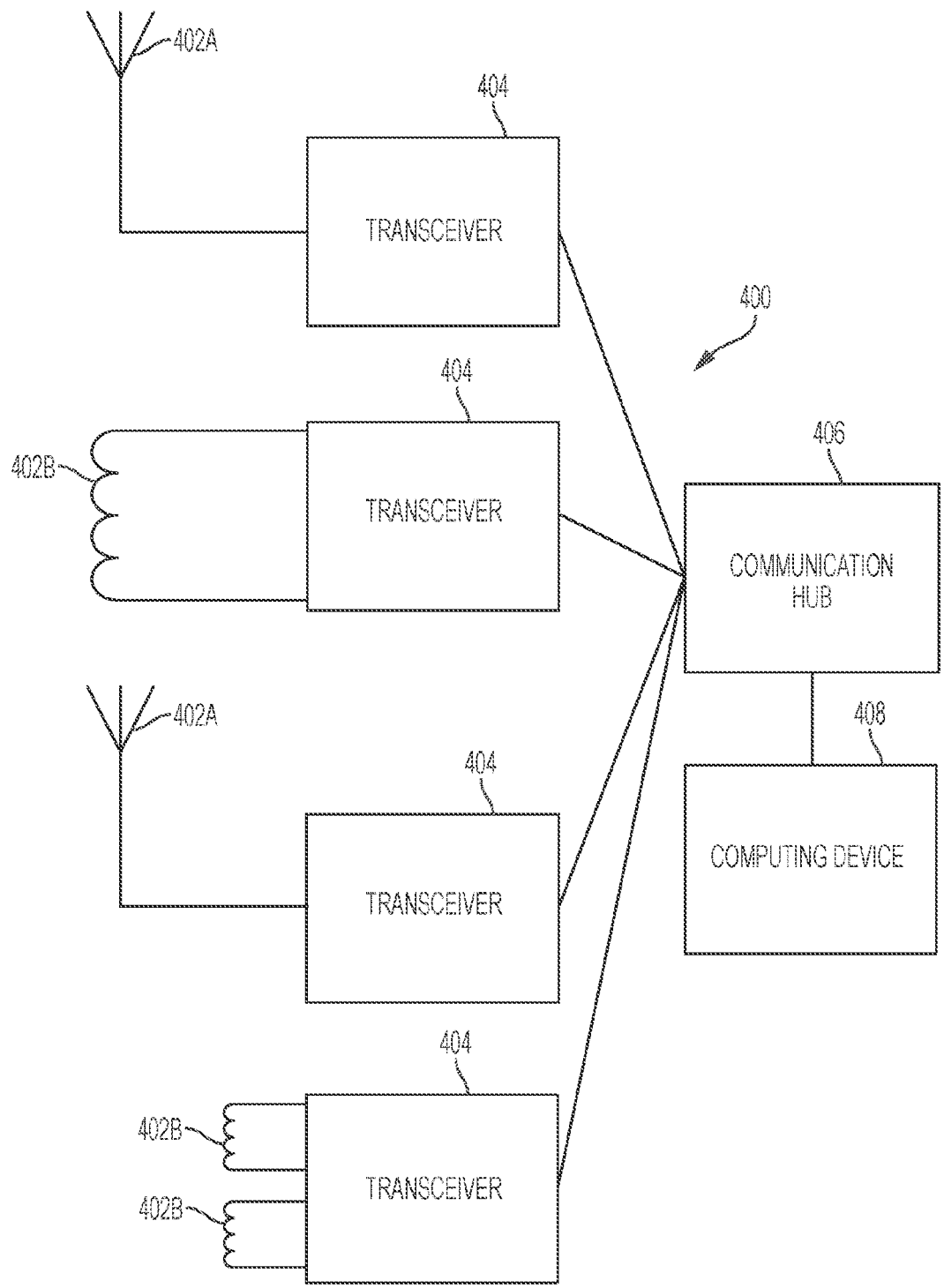
FIG. 4 is block system diagram of an integrated wireless environment, in an example embodiment.

FIG. 4 is block system diagram 400 of an integrated wireless environment, in an example embodiment. The block system diagram 400 describes a system that is configured to provide wireless communication with one or more articles of apparel 100 concurrently. The block system diagram 400 is scalable to include as many components as may be useful or necessary to provide desired bandwidth and spatial coverage within the integrated wireless environment.

The block system diagram 400 includes antennas 402, including first external antennas 402A, such as UHF antennas 402A, configured to communicate with the first antenna 118, and second external antennas 402B, such as HF antennas 402B, configured to communicate with the second antenna 120. In an example, sixteen antennas 402 are included in the system 400. It is to be recognized and understood that the particular modalities the antennas 402 are configured for may be selected based on the modal of the first and second antennas 118, 120. Furthermore, as various implementations of the wearable article 100 may utilize different modalities for the first and second antennas 118, 120, resulting in more than two modalities potentially home utilized within the integrated wireless environment at once, it is to be recognized and understood that the antennas 402 may be configured with three or more modalities.

Each antenna 402 is coupled to a wireless transceiver 404 configured transmit wireless signals to and receive wireless signals from one or both of the antennas 118, 120 via an associated one of the antennas 402. In various examples, multiple antennas 402 may be coupled to a single wireless transceiver 404. For instance, multiple HF antennas 402B that are collocated in a floor mat or other object may be coupled to a single wireless transceiver 404 which may allow those collocated antennas 402 to operate in close conjunction with one another. In an example, each antenna 402 is coupled to a wireless transceiver via a fifty Ohm cable. The wireless transceivers 404 are coupled to a communication hub 406. In various examples, the communication hub 406 is one or more of a universal serial bus (USB) hub, a wireless network router, a wired network router, and the like.

The communication hub 406 is coupled to a computing device 408, such as a personal computer, a server, and the like, configured to control the operation of the components of the system diagram 400. In an example, each wireless transceiver 404 is uniquely identified and independently addressable by the computing device 408. The computing device 408 is configured to independently select, activate, or deactivate each wireless transceiver 404.

The computing device 408 may incorporate two modes of operation of the wireless transceivers 404, a single mode and a continuous mode. In the single mode, a discrete command, whether entered by a user or based on a predetermined condition having been met, causes the computing device 408 to sequentially instruct the wireless transceivers 404 to power on art RF field via an associated antenna 402, attempt an interrogation, and then power the RF field off. In an example, only one wireless transceiver 404 is powered on at any given time. In an example, any or all HF antennas 402B nay be powered on at once while only one UHF antenna 402A may be powered on at once. Upon cycling through each wireless transceiver 404, the computing device 408 may catalog a unique identifier of each wearable article 100 interrogated by the wireless transceivers 404. By contrast, in the continuous mode, the computing device 408 continuously repeats the single mode cycles.

The computing device 408 includes a user interface 410 configured to display information and allow a user to set operating modes of the system. In an example, the user interface 410 is configured to display: a list of connected interrogated articles of apparel 100; connected articles of apparel 100 sensed wireless power levels (or received signal strength indication (RSSI)); which wireless transceiver 404 have connected with which articles of apparel 100; a unique identifier of each connected wearable article 100; and other information as may be desired. In an example, the user interface 410 is configured to allow a user to select: placing each wireless transceiver 404 individually in active or inactive mode; placing the system in single or continuous node; a system start for wireless interrogation, and a system stop for wireless interrogation. The user interface 410 may further include visual or audio indications of connecting with the wearable article 100, such as a tone, light, or other suitable mechanism.

The computing device 408 may include or may access a database including information regarding purchasers of the wearable article 100. The database may include as much information about such purchasers as may be accumulated within the bounds of privacy laws and other standards. Thus, the information on purchasers may include personal information, such as a name, age or age range, area of residence, personal activity (e.g., as obtained from an activity tracker device that may be included in the wearable article 100 or that may be included in a different device), personal purchase history or use of activities in or otherwise related to the integrated wireless environment, and credit card or other payment information from past purchases. The purchase history may include the wearable article 100 and/or any other items that may be entered into the database. The information included here is presented by way of illustration and not limitation and it is to be readily understood that the information that may be accessible by the computing device 408 may be expansive, as appropriate to the circumstances.

Figure 5:
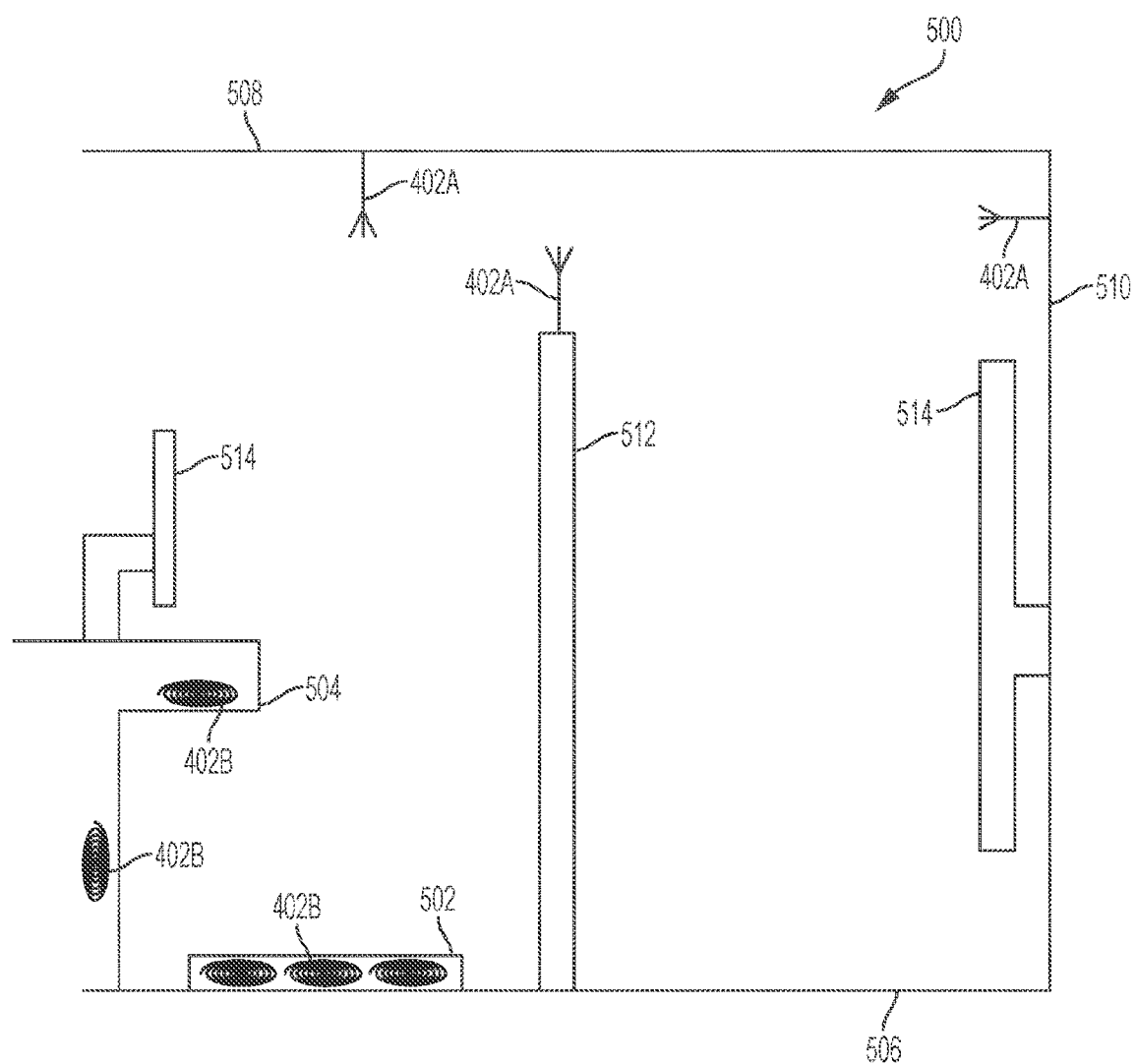
FIG. 5 is a side depiction of an integrated wireless environment, in an example embodiment.

FIG. 5 is a side depiction of an integrated wireless embodiment 500, in an example embodiment. The side depiction illustrates the relative positioning of antennas 402 within the integrated wireless environment 500 and is not necessarily representative of an actual layout of antennas 402 and other items within the integrated wireless environment 500.

In an example, the HF antennas 402B are seated or configured to be seated in a floor mat 502, a desk or a counter 504, or any object on, in, or within approximately one foot or thirty centimeters of a floor 506 or other walking surface.

The HF antennas 402B and the components coupled to and configured to utilize signals from the HF antennas 402B are configured to detect the presence of the second antenna 120 in communication proximity of an HF antenna 402B within approximately 0.5 seconds of the second antenna 120 coming into communication range of the HF antenna 402B. The UHF antennas 402A are positioned or configured to be positioned on a ceiling 508, wall 510, or support member 512 within approximately six to twenty feet or two to seven meters of a floor 506 or walking surface.

A user interface 514 is configured to display messages to a wearer of the wearable article 100 after one or more of the antennas 402 have connected with an antenna 118, 120 of the wearable article 100. A will be disclosed herein, the user interface 514 may be visible to the wearer of the wearable article 100 and may present messages related to the wearable article 100 or the wearer personally, including product or activity recommendations, directions within the integrated wireless environment, and so forth.

Figure 6:
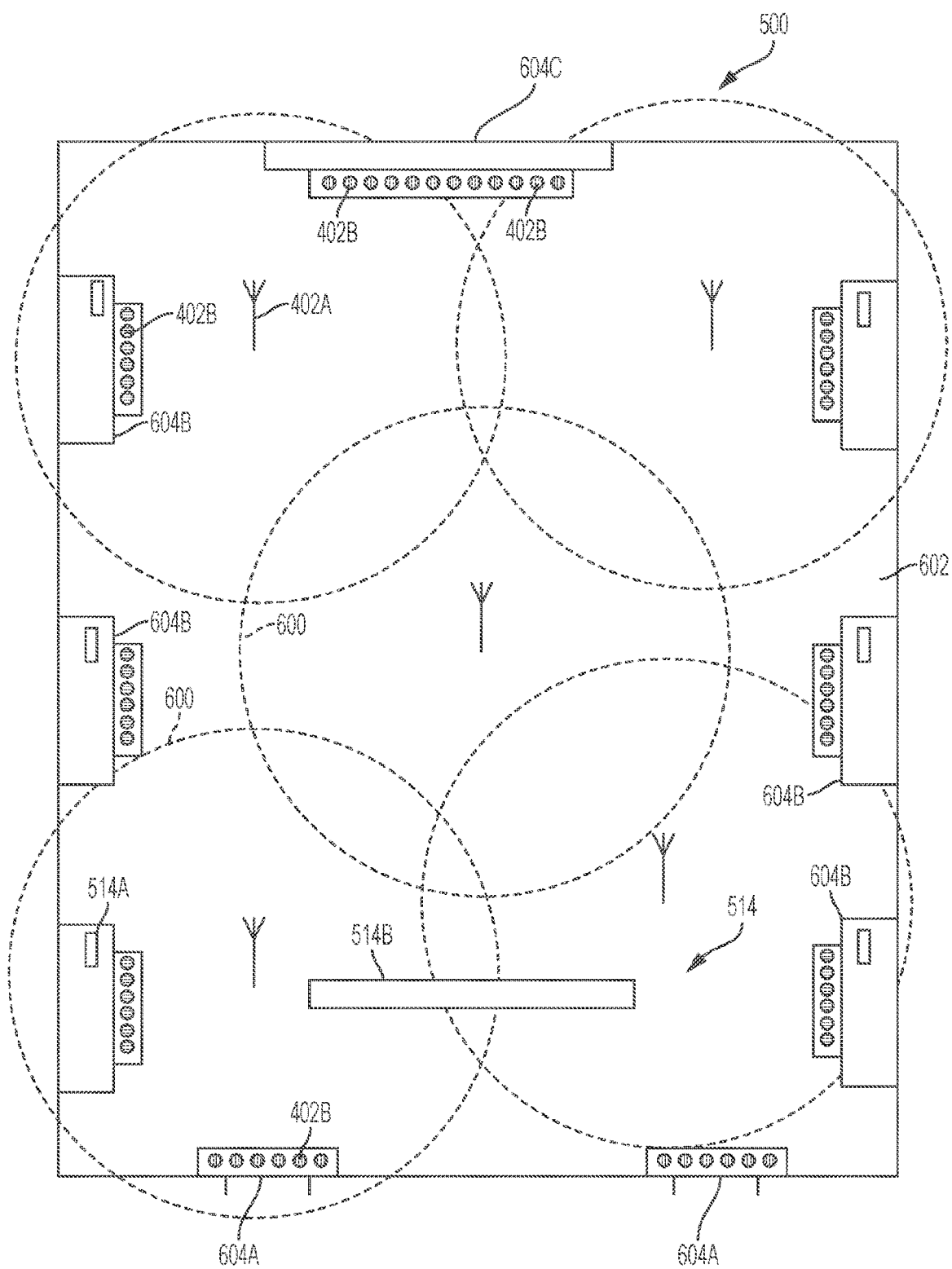
FIG. 6 is an overhead depiction of an integrated wireless environment, in an example embodiment.

FIG. 6 is an overhead depiction of the integrated wireless environment 500, in an example embodiment. The integrated wireless environment 500 as illustrated is a store or other commercial environment, though it is to be understood that the principles disclosed herein apply to any environment in which communication may be desired with the wearable article 100 being worn by people in the environment, such as sporting or cultural events. The integrated wireless environment 500 as illustrated is a space enclosed by walls 510, though it is to be understood that the integrated wireless environment 500 may include open-air spaces or spaces that are otherwise not clearly bounded.

The integrated wireless environment 500 includes general wireless coverage 600 provided by the UHF antennas 402A. The UHF antennas 402A are positioned throughout the integrated wireless environment 500 to provide such wireless coverage 600 substantially, though not necessarily completely, throughout the integrated wireless environment 500. As such, while "dead zones" 602 having no or unreliable wireless coverage may exist, in general as a wearer passes through the integrated wireless environment the first antenna 118 may always or substantially always be in communication with UHF antennas 402A.

The integrated wireless environment 500 further include local wireless coverage provided by the HF antennas 402B. Examples are contemplated in which HF antennas 402B may be spread throughout the integrated wireless environment 500 with a density such that HF communication may be generally available. As illustrated, however, HF coverage corresponds to discrete locations 604 in the integrated wireless environment 500. Examples of such discrete locations include doors 604A or other entrance/exit points, kiosks 604B for the presentation of various goods and services or the provision of games or information, and point of sale counters 604C or other interaction locations, among any of a variety of discrete locations that may be incorporated within an integrated wireless environment 500.

As illustrated, multiple HF antennas 402B are included in mats 502 or floor units in general, among other objects as disclosed herein. As the wearable article 100 passes over the mat 502 the second antenna 120 may come into communicative contact with some or all of the individual HF antennas 402B. Coming into communicative contact with any one or more of the individual HF antennas 402B may be sufficient to establish communication with the wearable article 100 for a discrete location 604.

The UHF antennas 402A may provide location information regarding the article of apparel. For instance, conventional triangulation techniques may be utilized in circumstances where multiple UHF antennas 402A cover the same area in the integrated wireless environment. At minimum, knowing which UHF antenna 402A is in communicative contact with the wearable article 100 allows the system 400 to know a general area in which the wearable article 100 is located.

In various examples, the UHF antennas 402A may provide general communication availability with the wearable article 100 while the HF antennas 402B provide location-specific communication with the wearable article 100. Thus, the HF antennas 402B may be utilized to identify when the wearable article 100 is in particular locations, i.e., the discrete locations 604, and provide for a direct experience for the wearer of the article of apparel, such as messages or other potential interactions with the wearer based on those discrete locations 604.

The integrated wireless environment 500 includes user interfaces 514, in the illustrated example. The user interfaces 514 include visual displays as well as optional audio or other sensory outputs. In various examples, the user interfaces 514 are comparatively small-scale 514A and designed to be viewed at a range of one or two meters or less and/or are large-scale 514B designed to be viewed at a range of six or seven meters or more.

In such examples, the UHF antennas 402A may provide general information about the presence and location of the wearable article 100. Interactions with the wearer of the wearable article 100 on the basis of information from the UHF antennas 402A may be in relatively large-scale user interfaces 514, such as visual and audio messages that may be suitable for experience not only by the wearer of the wearable article 100 but other people who may be in the vicinity of the wearer. For instance, the user interface 514 may, on the basis of communication via the UHF antennas 402A, display or otherwise broadcast a generic message complimenting the wearer for wearing the wearable article 100, offering a reward or discount on a purchase for wearing the wearable article 100, or other message that would not necessarily be viewed as private by most wearers of the wearable article 100.

By contrast, communication by the HF antenna 402B with the wearable article 100 may be utilized to produce small-scale experiences on user interfaces 514 at the discrete location 604 corresponding to the HF antenna 402B. Thus, the user interface 514 may display personalized greetings, information about the wearable article 100 and the wearer's use thereof that may not necessarily be for public consumption, such as a number of steps or other use-pattern information, suggested purchases or activities based on the use of the wearable article 100 and past purchases by the wearer, and so forth.

The HF antennas 402B may further be utilized to facilitate richer or additional interactions with the wearer of the wearable article 100. For instance, the computing device 408 may access the database corresponding to the purchaser of the wearable article 100 or a user to whom the ownership of the wearable article 100 has been transferred. If the data concerning the wearable article 100 includes credit card or bank account information the wearable article 100 may be utilized in conjunction with the HF antennas 402B to make purchases at kiosks 604B or point-of-sale counters 604C, whether by interacting directly with the user interlace 514 in that location 604 or by engaging in a predetermined activity with the wearable article 100 (e.g., tapping the wearable article 100 on the ground in a predetermined pattern, etc.).

Thus, in general, the UHF antennas 402A may be utilized to obtain a unique identification of the wearable article 100 to identify the presence of the wearable article 100 in the integrated wireless environment 500. The UHF antennas 402A may further facilitate general and relatively public interactions with the wearable article 100 and the wearer thereof. Privacy and anonymity may be of significant consideration in conducting such interactions.

By contrast, the HF antennas 402B may tend to provide for location tracking of the wearable article 100 between and among the discrete locations 604 and personalized interactions via the user interfaces 514 at those locations. The HF antennas 402B may facilitate providing personal information, such as sensor data from the wearable article 100, and personalized recommendations. Thus, the user interface 514 at one discrete location 604 may recommend for purchase a product at a different kiosk 604B based on the use pattern of the wearable article 100 as transmitted from the wearable article 100 to the computing device 408, whether directly or by way of the database, as disclosed herein.

Both the UHF antennas 402A and the HF antennas 402B are or may be configured to receive all of the same information from the wearable article 100. The corollary to that is both the first and second antennas 118, 120 are or may be configured to transmit all of the same information. However, the system 400 may be configured to utilize that information differently, allow different levels of access to additional information stored in databases, and/or restrict messages on the user interfaces 514 based on which of the antennas 402 are actually in communication with the wearable article 100.

Figure 7:
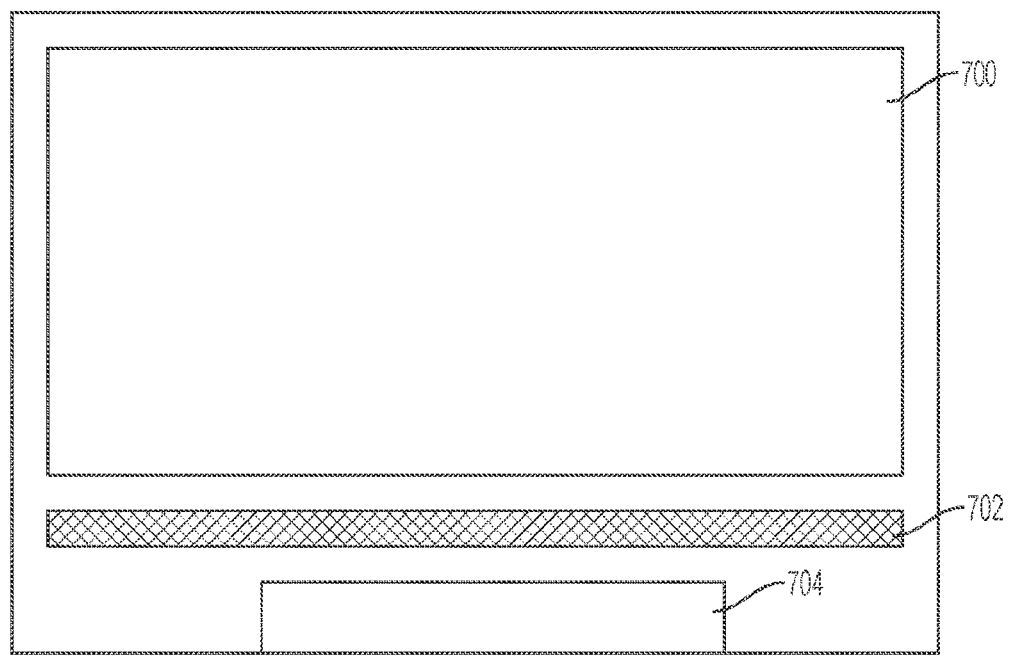
FIG. 7 is a depiction of a user interface, in an example embodiment.

FIG. 7 is a depiction of the user interface 514, in an example embodiment. The user interface 514 includes a visual display 700 and an audio emitter 702. In various examples, only one or the other of the visual display 700 and the audio emitter 702 are included. In an example, the user interface 514 includes a user input device 704, such as a touchscreen keyboard, or other electronic data entry systems.

As disclosed herein, the user interface 514 may be sized and implemented according to the circumstances in which the user interface 514 is used. Thus, the user interface 514 may be configured to be viewed or heard at some distance, such as a public video board that may be viewed throughout or from a large area of the integrated wireless environment 500. The user interface 514 may alternatively be sized, such as on a normal computer display or small television set, to be interacted with at a discrete location 604 in a way that may not be readily discerned by people in the area other than a specifically-intended recipient of a message.

The large-scale implementations of the user interface 514 may display or transmit audio messages that may be anonymous or that may convey lithe or no more information than may be readily publicly perceptible. Thus, when a UHF antenna 402A detects a wearable article 100 in the vicinity of the user interface 514, and the wearable article 100 is Model X shoe, the user interface 514 may display a message: "Nice Model X's. If you like those, you'll love the Model Y's right over here" and refer to a location 604 in the integrated wireless environment where the Model Y articles of apparel 100 can be obtained. Thus, the message from a generally viewed user interface 514 may not tend to directly identify the wearer of the wearable article 100 or give information other than what might be obtained simply by visually observing the wearable article 100 in use.

The small-scale implementation of the user interface 514 may display or otherwise convey the same or similar messages as the large-scale implementations. However, the small-scale implementation of the user interface 514 in conjunction with the localized HF antenna 402B communications may allow for more personal and private messages to be displayed. For instance, the message may include a personalized greeting: "Nice Model X's, John Doe. If you like those, . . . " The greetings may include information about the use of the article of apparel: "You've taken 250,000 steps in the last two months. Way to go!" or "You've taken 750,000 steps in our Model X's. You should think about a new pair."

The small-scale messages may be directly related to a proposed transaction. In various examples, the system 400 may allow purchases that are authenticated based on the identification of the wearable article 100. Thus, by obtaining the unique identifier of the wearable article 100, purchases may be made by a wearer of the wearable article 100 that may be charged to an associated credit card, bank account, or other financial implement. Thus, at a kiosk 604B, for instance, a wearer of the wearable article 100 may select a new product e.g., the Model Y's, variously by selecting the Model Y's is the user interface 514, by picking up the Model Y's and positioning them relative to an HF antenna 604, or by any other suitable mechanism. In such an example, the user interface 514 may prompt the wearer of the wearable article 100 whether or not the wearer wants to purchase the Model Y's and the wearer may variously accept or decline the transaction by using a touch interface or other user input device 704 or by otherwise engaging in an activity that may be detected by the system 400 and used to approve or reject the proposed transaction.

The messages that are described herein as being displayed may be provided to users in any suitable form including audio forms, such as spoken messages. Messages may include a combination of visual and audio prompts, among other sensory inputs. Thus, it is to be understood that the descriptions of the user interface 514 may extend to be relatively immersive or expansive multimedia presentations.

Figure 8:
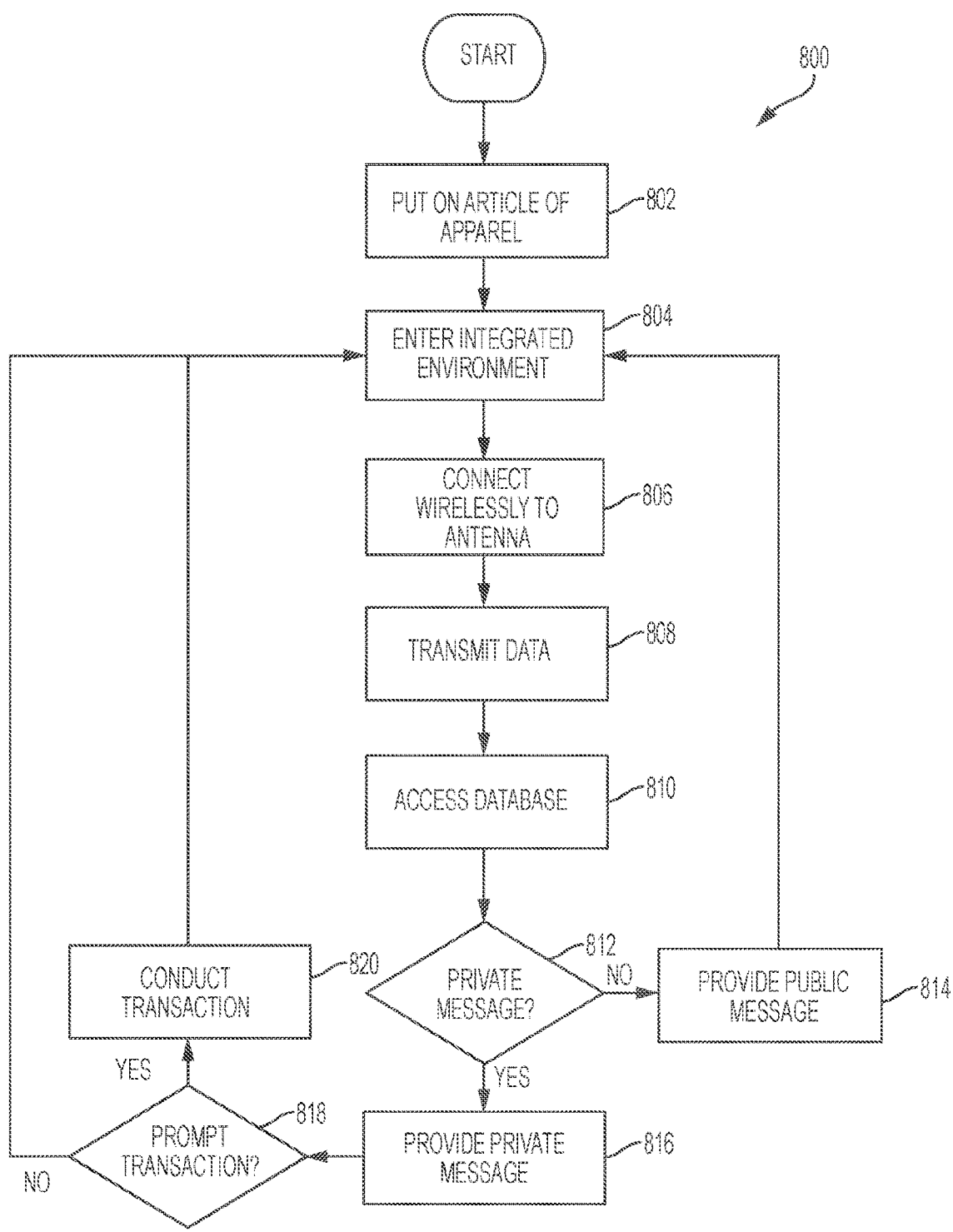
FIG. 8 is a flowchart for communicating between a wearable article and a wireless system in an integrated wireless environment, in an example embodiment.

FIG. 8 is a flowchart 800 for communicating between the wearable article 100 and the wireless system 400 in the integrated wireless environment 500, in an example embodiment. While the flowchart is described with respect to the wearable article 100 and the wireless system 400, it is to be understood that the operations in the flowchart may be implemented by any suitable devices and systems.

At 802, a wearer optionally puts on the wearable article 100. In an example where the wearable article 100 is a pair of shoes, the wearer secures the shoes to their feet. Thus, while not necessarily required, the following operations may be performed while the wearable article 100 is being worn and utilized in its conventional way.

At 804, the user of the wearable article 100 enters or approaches the integrated wireless environment 500. In an example, the user enters by walking or otherwise passing through the entrance 604A.

At 806, the wireless system 400 connects wirelessly according to one or more of the wireless modalities supported by the first and second antennas 118, 120. In various examples, the first antenna 118 communicates according to a UHF modality and wirelessly connects with at least one UHF antenna 402A. In various examples, upon first entering or leaving the integrated wireless environment 500, the second antenna 120 communicates according to an HF modality and wirelessly connects with at least one HF antenna 402B positioned in a floor mat 502 positioned at the entrance 604A. As the user moves around the integrated wireless environment 500, different and/or additional antennas 402 may connect wirelessly with the antennas 118, 120 of the wearable article 100.

At 808, the wearable article 100 transmits data from the electronic data storage 128 to the wireless system 400. The data includes a unique identifier of the wearable article 100 as well as any additional information as may be appropriate, as disclosed herein. In an example, the additional information includes use information of the wearable article 100. In an example where the wearable article 100 is one or more shoes, the additional information may be a number of steps taken in the wearable article 100 and a time and manner of use of the wearable article 100.

At 810, the computing device 408 accesses a database based on the unique identifier of the article of apparel and obtains information about the wearable article 100. Such information may include a make and model of the wearable article 100, an identification of a purchaser of the wearable article 100, a current owner or user associated with the wearable article 100 if different from the purchaser, a purchase history of the purchaser and/or owner, previously obtained use information of the wearable article 100 and other items that have been purchased by the purchaser/user demographic information of the purchaser/user and so forth.

At 812, the computing device 408 determines if messages or other interactions with the user of the wearable article 100 should be private. The determination may be based, at least in part, on the wireless modality of the antenna 402 that has made connected with the wearable article 100. Thus, in an example, if the modality is relatively long range UHF communications then the interactions are not private and the flowchart 800 proceeds to 814. If the modality is relatively short range HF communications then the interactions should be private and the flowchart proceeds to 816.

At 814, the computing device 408 causes a user interface 514 to display of otherwise provide a public or otherwise non-private, large-scale message to the user. The non-private or otherwise public message may be displayed or otherwise provided on or by a large-scale user interface 600. As disclosed herein, such messages may include relatively little or no personal or private information about the user of the wearable article 100 that the user may not desire to be seen by other people who are in the integrated wireless environment 500. After displaying the public message, the flowchart 800 may proceed back to 806 and wait for a further wireless connection with the wearable article 100.

At 810, the computing device 408 causes a user interface 514 to display or otherwise provide a private or otherwise non-public, small-scale message to the user. The message may be displayed or otherwise provided on or by a small-scale user interface 600. The private message may include personal information about the user or information that the user does not necessarily want to be seen by other people.

At 818, the computing device 408 may determine if a transaction, such as purchasing an item or service at a kiosk 604B, should be prompted or otherwise initiated. In an example, the determination may be automatic to prompt a user at a kiosk 604B. Alternatively, the determination may be based on factors relating to the user and the wearable article 100. For instance, the determination may be based on the wearable article 100 being recommended for replacement or based on demographic and purchase history of the user. Further alternatively, the determination may be based on a request by the user to begin a transaction via the user interface 514. If the computing device 408 determines that a transaction should not be prompted then the flowchart 800 proceeds back to 806 and wait for a further wireless connection with the wearable article 100.

At 820, if a transaction is prompted, the computing device 408 conducts the transaction based at least in part, on authentication of the transaction based on the unique identifier of the wearable article 100 previously obtained from the article of apparel at 808. The flowchart 800 proceeds back to 806 and wait for a further wireless connection with the wearable article 100.

Figure 9:
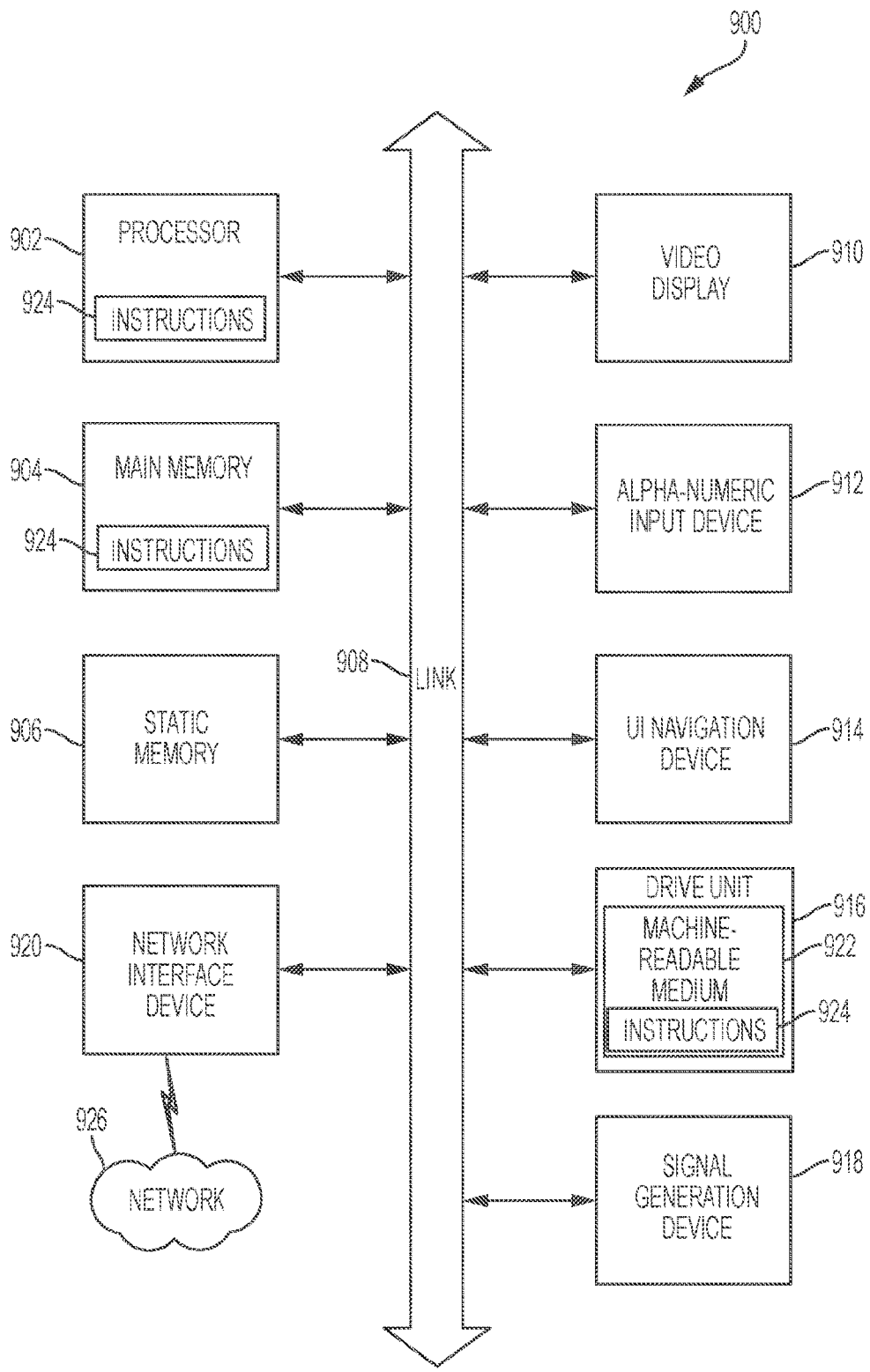
FIG. 9 is a block diagram illustrating components of a machine, according to some example embodiments, able to read instructions from a machine-readable medium.

FIG. 9 is a block diagram illustrating components of a machine 900, according to some example embodiments, able to read instructions from a machine-readable medium (e.g., a machine-readable storage medium) and perform any one or more of the methodologies discussed herein. Specifically, FIG. 9 shows a diagrammatic representation of the machine 900 in the example form of a computer system and within which instructions 924 (e.g., software) for causing the machine 900 to perform any one or more of the methodologies discussed herein may be executed. In alternative embodiments, the machine 900 operates as a standalone device or may be connected (e.g., networked) to other machines. In a networked deployment, the machine 900 may operate in the capacity of a server machine or a client machine in a server-client network environment, or as a peer machine in a peer-to-peer (or distributed) network environment. The machine 900 may be a server computer, a client computer, a personal computer (PC), a tablet computer, a laptop computer, a netbook, a set-top box (STB), a personal digital assistant (PDA), a cellular telephone, a smartphone, a web appliance, a network router, a network switch, a network bridge, or any machine capable of executing the instructions 924, sequentially or otherwise, that specify actions to be taken by that machine. Further, while only a single machine is illustrated, the term "machine" shall also be taken to include a collection of machines that individually or jointly execute the instructions 924 to perform any one or more of the methodologies discussed herein.

The machine 900 includes a processor 902 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 904, and a static memory 906, which are configured to communicate with each other via a bus 908. The machine 900 may further include a graphics display 910 (e.g., a plasma display panel (PDP), a light emitting diode (LED) display, a liquid crystal display (LCD), a projector, or a cathode is tube (CRT)). The machine 900 may also include an alphanumeric input device 912 (e.g., a keyboard), a cursor control device 914 (e.g., a mouse, a touchpad, a trackball, a joystick, a motion sensor, or other pointing instrument), a storage unit 916, a signal generation device 912 (e.g., a speaker), and a network interface device 920.

The storage unit 916 includes a machine-readable medium 922 on which is stored the instructions 924 (e.g., software) embodying any one or more of the methodologies or functions described herein. The instructions 924 may also reside, completely or at least partially, within the main memory 904, within the processor 902 (e.g., within the processor's cache memory), or both, during execution thereof by the machine 900. Accordingly, the main memory 904 and the processor 902 may be considered as machine-readable media. The instructions 924 may be transmitted or received over a network 926 via the network interface device 920.

As used herein, the term "memory" refers to a machine-readable medium able to store data temporarily or permanently and may be taken to include, but not be limited to, random-access memory (RAM), read-only memory (ROM), buffer memory, flash memory, ferroelectric RAM (FRAM), and cache memory. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., software) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one of more data repositories in the form of a solid-state memory, an optical medium, a magnetic medium, or any suitable combination thereof.

EXAMPLES

In Example 1, an article of apparel optionally includes a structure configured to enclose a human body part, first antenna, positioned with respect to the structure, tuned to communicate, while the article of apparel is being worn, according to a first wireless communication modality with a first external antenna, a second antenna, positioned with respect to the structure, tuned to communicate according to a second wireless communication modality with a second external antenna different than the first external antenna, the second communication modality being different than the first communication modality, and a transceiver, operatively coupled to at least one of the first antenna and the second antenna, configured to communicate via one of the first and second antennas based, at least in part, on the one of the first and second antennas coming into wireless communication contact with a corresponding one of the first and second external antennas.

In Example 2, the article of apparel of Example 1 optionally further includes that the first wireless communication modality, is an ultra high frequency (UHF) communication modality.

In Example 3, the article of apparel of any one or more of Examples 1 and 2 optionally further includes that the second wireless communication modality is a high frequency (HF) communication modality.

In Example 4, the article of apparel of any one or more of Examples 1-3 optionally further includes an electronic data storage, operatively coupled to the transceiver, the electronic data storage configured to store a unique identifier associated with the article of apparel, and wherein the transceiver is configured to transmit the unique identifier upon communicating via the one of the first and second antennas.

In Example 5, the article of apparel of any one or more of Examples 1-4 optionally further includes that the electronic data storage is further configured to store information generated by the use at the article of apparel related to the use of the article of apparel.

In Example 6, the article of apparel of any one or more of Examples 1-5 optionally further includes that the article of apparel is an article of footwear and wherein the indication generated by the use of the article of apparel are steps taken in the article of footwear.

In Example 7, the article of apparel of any one or more of Examples 1-6 optionally further includes that the article of apparel is an article of footwear, wherein the structure includes a heel of the article of footwear, and wherein the first antenna is located in the heel.

In Example 8, the article of apparel of any one or more of Examples 1-7 optionally further includes that the article of apparel is an article of footwear, wherein the structure includes a sole of the article of footwear, and wherein the first antenna is located in the sole.

In Example 9, the article of apparel of any one or more of Examples 1-8 optionally further includes that the article of apparel comprises a decorative element comprising the first antenna.

In Example 10, the article of apparel of any one or more of Examples 1-9 optionally further includes that the decorative element further comprises the second antenna.

In Example 11, the article of apparel of any one or more of Examples 1-10 optionally further includes that the article of apparel is an article of footwear, wherein the structure includes a tongue of the article of footwear, and wherein the second antenna is located in the tongue.

In Example 12, a system optionally includes a first external antenna tuned to communicate with a first antenna of an article of apparel according to a first wireless communication modality while the article of apparel is being worn, a second external antenna tuned to communicate with a second antenna of the article of apparel according to a second wireless communication modality different than the first communication modality, a transceiver, operatively coupled to at least one of the first antenna and the second antenna, configured to communicate via one of the first and second antennas based, at least in part, on the one of the first and second antennas coming into wireless communication contact with a corresponding one of the first and second external antennas and receive from the article of apparel, a unique identifier of the article of apparel, and a computing device configured to receive the unique identifier and cause a user interface to provide a message based, at least in part, on the unique identifier.

In Example 13, the system of Example 12 optionally further includes that the computing device is further configured to cause the user interface to provide the message based on the at least one of the first antenna and the second antenna that comes into wireless communication contact with the corresponding one of the first and second antennas.

In Example 14, the system of any one or more of Examples 12 and 13 optionally further includes that the computing device is confirmed to cause the user interface to provide a public message based on wireless communication via the first antenna and a private message based on wireless communication via the second antenna.

In Example 15, the system of any one or more of Examples 12-14 optionally further includes that the first wireless communication modality is an ultra high frequency (UHF) communication modality.

In Example 16, the system of any one or more of Examples 12-15 optionally further includes that the article of apparel is an article of footwear and wherein the first external antenna is positioned on at least one of a wall and a ceiling.

In Example 17, the system of any one or more of Examples 12-16 optionally further includes that the second wireless communication modality is a high frequency (HF) communication modality.

In Example 18, the system of any one or more of Examples 12-17 optionally further includes that the second external antenna is positioned within approximately one (1) foot of a walking surface.

In Example 18, the system of any one or more of Examples 12-17 optionally further includes that the article of apparel is an article of footwear and wherein the second external antenna is positioned within at least one of a walking surface and a floor mat configured to be walked on by the article of apparel.

In Example 19, the system of any one or more of Examples 12-18 optionally further includes that the article of apparel is an article of footwear and wherein the second external antenna is positioned within at least one of a walking surface and a floor mat configured to be walked on by the article of apparel.

In Example 20, the system of any one or more of Examples 12-19 optionally further includes that wherein a plurality of second external antennas are positioned within the at least one of the walking surface and the floor mat and each of the plurality of second external antennas are configured to communicate with the second antenna.

In Example 21, the system of any one or more of Examples 12-20 optionally further includes that the second external antenna corresponds to a discrete location and wherein, upon the transceiver communicating with the second antenna via the second external antenna, the article of apparel is determined to be substantially at the discrete location.

In Example 22, the system of any one or more of Examples 12-21 optionally further includes the user interface, wherein the user interface is positioned in proximity of the discrete location, wherein the computing device is configured to cause the message to be displayed based on the article of apparel being substantially at the discrete location.

In Example 23, the system of any one or more of Examples 12-22 optionally further includes a plurality of transceivers, including the transceiver, coupled to the computing device, wherein a first one of the plurality of transceivers is coupled to the first external antenna and configured to communicate according to the first wireless modality and a second one of the plurality of transceivers is coupled to the second external antenna and configured to communicate according to the second wireless modality.

In Example 24, a method optionally includes enclosing, with a structure of an article of apparel, a human body part, communicating wirelessly, using a transceiver, with a first antenna, positioned with respect to the structure, while the article of apparel is being worn, according to a first wireless communication modality with a first external antenna based on the first antenna coining into wireless communication contact with the first external antenna, and communicating wirelessly, using the transceiver, with a second antenna, positioned with respect to the structure, tuned to communicate according to a second wireless communication modality with a second external antenna different than the first external antenna, the second communication modality being different than the first communication modality, based on the second antenna coming into wireless communication contact with the second external antenna.

In Example 25, the method of Example 24 optionally further includes that the first wireless communication modality is an ultra high frequency (UHF) communication modality.

In Example 26, the method of any one or more of Examples 24 and 25 optionally further includes that the second wireless communication modality is a high frequency (HF) communication modality.

In Example 27, the method of any one or more of Examples 24-26 optionally further includes storing, with a processor, in an electronic data storage, a unique identifier associated with the article of apparel, and transmitting, using the transceiver, the unique identifier upon communicating via the one of the first and second antennas.

In Example 28, the method of any one or more of Examples 24-27 optionally further includes storing, with the processor, in the electronic data storage, information generated by the use of the article of apparel related to the use of the article of apparel.

In Example 29, the method of any one of more of Examples 24-28 optionally further includes that the article of apparel is an article of footwear and wherein the indication generated by the use of the article of apparel are steps taken in the article of footwear.

In Example 30, the method of any one or more of Examples 24-29 optionally further includes that the article of apparel is an article of footwear, wherein the structure includes a sole of the article of footwear, and wherein the first antenna is located at the heel.

In Example 31, the method of any one or more of Examples 24-30 optionally further includes that the article of apparel is an article of footwear, wherein the structure includes a sole of the article of footwear, and wherein the first antenna is located in the sole.

In Example 32, the method of any one or more of Examples 24-31 optionally further includes that the article of apparel comprises a decorative element comprising the first antenna.

In Example 33, the method of any one or more of Examples 24-32 optionally further includes that the decorative element further comprises the second antenna.

In Example 34, the method of any one or more of Examples 24-33 optionally further includes that the article of apparel is an article of footwear, wherein the structure includes a tongue of the article of footwear, and wherein the second antenna is located in the tongue.

In Example 35, a method optionally includes communicating, using a transceiver and a first external antenna, with a first antenna of an article of apparel according to a first wireless communication modality while the article of apparel is being worn based, at least in part, on the first antenna coming into wireless communication contact with the first external antenna, communicating, using a transceiver and a second external antenna, with a second antenna of the article of apparel according to a second wireless communication modality different than the first communication modality based, at least in part, on the second antenna coming into wireless communication contact with the second external antenna, receiving, with a computing device, from the article of apparel, via the transceiver, a unique identifier of the article of apparel, and causing, with the computing device, a user interface to provide a message based, at least in part, on the unique identifier.

In Example 36, the method of Example 35 optionally further includes causing, with the computing device, the user interface to provide the message based on at least one of the first antenna and the second antenna that comes into wireless communication contact with the corresponding one of the first and second antennas.

In Example 37, the method of any one or more of Examples 35 and 36 optionally further includes causing, with the computing device the user interface to provide a public message based on wireless communication via the first antenna and a private message based on wireless communication via the second antenna.

In Example 38, the method of any one or more of Examples 35-37 optionally further includes that the first wireless communication modality is an ultra high frequency (UHF) communication modality.

In Example 39, the method of any one or more of Examples 35-38 optionally further includes that the article of apparel is an article of footwear and wherein the first external antenna is positioned on at least one of a wall and a ceiling.

In Example 40, the method of any one or more of Examples 35-39 optionally further includes that the second wireless communication modality is a high frequency (HF) communication modality.

In Example 41, the method of any one or more of Examples 35-40 optionally further includes that the second external antenna is positioned within approximately one (1) foot of a walking surface.

In Example 42, the method of any one or more of Examples 35-41 optionally further includes that the article of apparel is an article of footwear and wherein the second external antenna is positioned within at least one of a surface and a floor mat configured to be walked on by the article of apparel.

In Example 43, the method of any one or more of Examples 35-42 optionally further includes that a plurality of second external antennas are positioned within the least one of the walking surface and the floor mat and each of the plurality of second external antennas are configured to communicate with the second antenna.

In Example 44, the method of any one or more of Examples 35-43 optionally further includes that the second external antenna corresponds to a discrete location and further comprising determining, upon the transceiver communicating with the second antenna via the second external antenna, the article of apparel to be substantially at the discrete location.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations of functions described herein. As used herein "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an application program interface (API)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content" "bits," "values," "elements," "symbols," "characters," "terms," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

What is claimed is:
1. A system, comprising:
an external antenna tuned to communicate with an antenna of a wearable article according to a wireless communication modality while the wearable article is being worn;

a transceiver, operatively coupled to and configured to communicate via the external antenna according to the communication modality;

a user interface, configured to present a message to a wearer of the wearable article; and a computing device, operatively coupled to the transceiver and to the user interface, configured to:

receive an output signal from the transceiver;

determine that the signal from the transceiver is a valid communication signal according to the communication modality and indicative that the external antenna has come into wireless communication contact with the antenna of the wearable device; and upon determination of the valid communication signal, cause the transceiver to activate the external antenna and communicate between the external antenna and the antenna of the wearable device;

receive a unique identifier from the wearable article; and cause the user interface to present the message based, at least in part, on the unique identifier.

2. The system of claim 1, wherein the message includes at least one of a visual component or an audio component.

3. The system of claim 1, wherein the message is a personalized message to the wearer of the wearable article.

4. The system of claim 3, wherein the personalized message is related to the wearable article.

5. The system of claim 3, wherein the personalized message is an offer to purchase an article different than the wearable article.

6. The system of claim 3, wherein the personalized message is a prompt to the wearer to engage in a predetermined activity with the wearable article.

7. The system of claim 3, wherein the personalized message is a recommendation regarding the wearable article.

8. The system of claim 7, wherein the recommendation relates to remaining wear on the wearable article.

9. The system of claim 3, wherein the personalized message relates to an amount the wearable article has been used.

10. The system of claim 1, wherein the message is a public message configured to be presented to multiple people in the vicinity of the user interface.

11. A method, comprising:

receiving, at a transceiver, via an external antenna, a wireless signal, the external antenna tuned to communicate with an antenna of a wearable article according to a wireless communication modality while the wearable article is being worn;

receiving, with a computing device, an output signal from the transceiver;

determining, with the computing device, that the signal from the transceiver is a valid communication signal according to the communication modality and indicative that the external antenna has come into wireless communication contact with the antenna of the wearable device; and upon determination of the valid communication signal, causing, with the computing device, the transceiver to activate the external antenna and communicate between the external antenna and the antenna of the wearable device:

receiving, with the computing device, a unique identifier from the wearable article; and causing, with the computing device, a user interface to present the message based, at least in part, on the unique identifier.

12. The method of claim 11, wherein the message includes at least one of a visual component or an audio component.

13. The method of claim 11, wherein the message is a personalized message to the wearer of the wearable article.

14. The method of claim 13, wherein the personalized message is related to the wearable article.

15. The method of claim 13, wherein the personalized message is an offer to purchase an article different than the wearable article.

16. The method of claim 13, wherein the personalized message is a prompt to the wearer to engage in a predetermined activity with the wearable article.

17. The method of claim 13, wherein the personalized message is a recommendation regarding the wearable article.

18. The method of claim 17, wherein the recommendation relates to remaining wear on the wearable article.

19. The method of claim 13, wherein the personalized message relates to an amount the wearable article has been used.

20. The method of claim 11, wherein the message is a public message configured to be presented to multiple people in the vicinity of the user interface.

* * * * *